(12) United States Patent
Han et al.

(10) Patent No.: US 10,484,780 B2
(45) Date of Patent: Nov. 19, 2019

(54) AUDIO OUTPUT APPARATUS AND METHOD FOR OPERATING AUDIO OUTPUT APPARATUS

(71) Applicant: Samsung Electronics Co., Ltd., Gyeonggi-do (KR)

(72) Inventors: Sang Woo Han, Gyeonggi-do (KR); Ji Ho Lee, Seoul (KR); Hyun Jung Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 16/390,608

(22) Filed: Apr. 22, 2019

(65) Prior Publication Data

US 2019/0246196 A1    Aug. 8, 2019

Related U.S. Application Data

(63) Continuation of application No. 15/399,140, filed on Jan. 5, 2017, now Pat. No. 10,313,776.

(30) Foreign Application Priority Data

Jan. 5, 2016    (KR) .................. 10-2016-0001153

(51) Int. Cl.
  *H04R 1/10*    (2006.01)
  *G06F 3/01*    (2006.01)
  (Continued)

(52) U.S. Cl.
  CPC ....... *H04R 1/1041* (2013.01); *A61B 5/02438* (2013.01); *A61B 5/6803* (2013.01);
  (Continued)

(58) Field of Classification Search
  CPC ............. H04R 1/1041; H04R 2420/07; H04R 1/1016; G06F 3/0481; G06F 3/0488;
  (Continued)

(56) References Cited

U.S. PATENT DOCUMENTS 8,045,727 B2    10/2011  Phillip
2007/0121959 A1    5/2007  Phillip
(Continued)

FOREIGN PATENT DOCUMENTS

JP    2011114677    6/2011
KR    100617576    9/2006

*Primary Examiner* — Paul Kim
(74) *Attorney, Agent, or Firm* — The Farrell Law Firm, P.C.

(57) ABSTRACT

Systems, methods, and audio output devices are described. In one aspect, an audio output device includes a communication module that communicates with an external electronic device, a speaker that outputs sound, a mounting detection sensor that detects whether the audio output device is mounted on a user of the audio output device, and a control circuit that is electrically connected with the communication module, the speaker, and the mounting detection sensor. The control circuit wirelessly connects the external electronic device with the audio output device using the communication module if the mounting of the audio output device is detected by the mounting detection sensor, receives audio data from the external electronic device through the wireless connection, and outputs the audio data using the speaker.

20 Claims, 6 Drawing Sheets

(51) Int. Cl.
*A61B 5/00* (2006.01)
*G06F 3/0481* (2013.01)
*G06F 3/0488* (2013.01)
*A61B 5/024* (2006.01)

(52) U.S. Cl.
CPC ............ *A61B 5/6817* (2013.01); *G06F 3/011* (2013.01); *G06F 3/0481* (2013.01); *G06F 3/0488* (2013.01); *H04R 1/1016* (2013.01); *A61B 5/6844* (2013.01); *H04R 2420/07* (2013.01)

(58) Field of Classification Search
CPC . A61B 5/6817; A61B 5/02438; A61B 5/6803; A61B 5/6844
USPC .......................................................... 381/74
See application file for complete search history.

(56) References Cited

U.S. PATENT DOCUMENTS

2012/0244812 A1* 9/2012 Rosener .................. H04M 1/05 455/41.3
2015/0309316 A1* 10/2015 Osterhout ............... G06F 1/163 345/8

* cited by examiner

AUDIO OUTPUT APPARATUS AND METHOD FOR OPERATING AUDIO OUTPUT APPARATUS

PRIORITY

This application is a Continuation Application of U.S. application Ser. No. 15/399,140, filed in the U.S. Patent and Trademark Office (USPTO) on Jan. 5, 2017, which claims priority under 35 U.S.C. § 119(a) to a Korean Patent Application filed on Jan. 5, 2016 in the Korean Intellectual Property Office and assigned Serial number 10-2016-0001153, the entire disclosure of which is incorporated herein by reference.

BACKGROUND

1. Field of the Disclosure

The present disclosure relates generally to a method for controlling the operation of an audio output device, and more particularly, to a method for controlling the operation of an audio output device based on the mounting of the audio output device on the user of the audio output device.

2. Description of the Related Art

With the development of the electronic communication industry, user devices have become the must-have item of modern society and an important means for information delivery, the technology of which is changing rapidly. Recently, user devices have been developed in various forms that are worn, attached to, and/or mounted on a user's body in order to provide improved portability and user accessibility.

Such user devices include, for example, wireless audio output devices (e.g., wireless earphones/headphones), which are implemented to be inserted into or to be closely attached to a user's ear. Wireless audio output devices may be wirelessly connected with external electronic devices, such as, e.g., a smartphone or a tablet personal computer (PC). The wireless audio output device may require user manipulation in order to connect with the external electronic device. For this reason, the user may manipulate the wireless audio output device or the external electronic device upon connection. Furthermore, in the case where the wireless audio output device is equipped with a touch pad, a wrong input to the touch pad may be generated when the user is mounting the wireless audio output device on his/her body.

SUMMARY

Aspects of the present disclosure are to address at least the above-mentioned problems and/or disadvantages and to provide at least the advantages described below. Accordingly, an aspect of the present disclosure is to provide an audio output device and a method that make it possible to automatically connect with an external electronic device when mounting and to prevent a wrong input to the touch pad from being generated when mounting.

In accordance with an aspect of the present disclosure, an audio output device includes a communication module that communicates with an external electronic device, a speaker that outputs sound, a mounting detection sensor that detects whether the audio output device is mounted on a user of the audio output device, and a control circuit that is electrically connected with the communication module, the speaker, and the mounting detection sensor, wherein the control circuit connects the external electronic device with the audio output device in wireless communication using the communication module if the mounting of the audio output device is detected by the mounting detection sensor, receives audio data from the external electronic device through the wireless communication, and outputs the audio data using the speaker.

In accordance with an aspect of the present disclosure, an operating method of an audio output device includes wirelessly connecting an external electronic device with the audio output device, if mounting of the audio output device on a user of the audio output device is detected, receiving audio data from the external electronic device through the wireless connection, and outputting the audio data.

In accordance with an aspect of the present disclosure, an audio output device includes a first output device and a second output device. The first output device includes a first communication module that communicates with an external electronic device and the second output device, a first speaker that outputs sound, a mounting detection sensor that detects mounting of the first output device to a user of the audio output device, and a first control circuit that is electrically connected with the first communication module, the first speaker, and the mounting detection. The first control circuit wirelessly connects, if mounting of the first output device is detected by the mounting detection sensor, the external electronic device with the first output device in a first wireless communication connection using the first communication module, receives audio data from the external electronic device through the first wireless communication connection, sends at least a portion of the audio data to the second output device through a second wireless communication, and outputs at least a portion of the audio data using the first speaker. The second output device includes a second communication module that communicates with the first output device, a second speaker that outputs sound, and a second control circuit that is electrically connected with the second communication module and the second speaker. The second control circuit receives the at least a portion of the audio data from the first output device through the second wireless communication connection using the second communication module, and outputs the at least a portion of the audio data using the second speaker.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Various embodiments of the present disclosure are described herein with reference to accompanying drawings. Those of ordinary skill in the art will recognize that modifications to, equivalents of, and/or alternatives to the various embodiments described herein can be variously made/used without departing from the scope and spirit of the present disclosure. With regard to the drawings, similar elements may be marked by similar reference numerals.

The expressions "have", "may have", "include" and "comprise", or "may include" and "may comprise" as used herein indicate the existence of corresponding listed features (e.g., elements such as numeric values, functions, operations, or components) but do not exclude presence of additional features. The expressions "A and/or B", "at least one of A and/or B", or "one or more of A and/or B", and the like as used herein may include any and all combinations of one or more of the listed items. For example, the terms "A and/or B", "at least one of A and B", or "at least one of A or B" includes (1) at least one A, (2) at least one B, and/or (3) of at least one A and at least one B. Terms such as "first", "second", and the like as used herein to refer to various elements of various embodiments of the present disclosure do not limit those elements or embodiments. For example, "a first user device" and "a second user device" may indicate different user devices regardless of their specific order or priority (if any). As such, a first element may be referred to as a second element, and similarly, a second element may be referred to as a first element.

Depending on the context/situation, when an element (e.g., a first element) is referred to herein as being "operatively (or communicatively) coupled with/to" or "connected to" another element (e.g., a second element), it may be directly coupled with/to or connected to the other element or there may be one or more intervening third elements. By contrast, when an element (e.g., a first element) is referred to herein as being "directly coupled with/to" or "directly connected to" another element (e.g., a second element), there are no intervening third elements.

According to the context/situation, the expression "configured to" as used herein may be used interchangeably with, for example, any of the expressions "suitable for", "having the capacity to", "designed to", "adapted to", "made to", or "capable of". The expression "configured to" as used herein does not mean "specifically designed to" in hardware. Instead, the expression "a device configured to" may mean that the device is "capable of" performing the corresponding listed operation(s). For example, a "processor configured to perform A, B, and C" may include both a dedicated processor (e.g., an embedded processor) for performing the corresponding listed operation(s) and a generic or general-purpose processor (e.g., a central processing unit (CPU) or an application processor) which may perform the corresponding listed operation(s) by executing one or more software programs which are stored in a memory device.

Terms used in this disclosure to describe specific embodiments of the present disclosure are not intended to limit the scope of the present disclosure. The terms in singular form may include plural forms unless otherwise specified. All the terms used herein, which include technical or scientific terms, may have the same meaning as that which is generally understood by a person skilled in the art. It will be further understood that terms, which are defined in a dictionary and commonly used, should also be interpreted as is customary in the relevant related art and not in an idealized or overly formal manner unless expressly defined so herein. In some cases, even with terms which are defined in the disclosure, those terms may not be interpreted to exclude embodiments of the present disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, a wearable device may include at least one of an accessory type (e.g., watches, rings, bracelets, anklets, necklaces, glasses, contact lens, or head-mounted-devices (HMDs), a fabric or garment-integrated type (e.g., electronic apparel), a body-attached type (e.g., a skin pad or tattoo), or an implantable type (e.g., an implantable circuit).

According to various embodiments, the electronic device may be a home appliance. Such home appliances may include at least one of, for example, televisions (TVs), digital versatile disc (DVD) players, audio players, refrigerators, air conditioners, cleaners, ovens, microwave ovens, washing machines, air cleaners, set-top boxes, TV boxes (e.g., Samsung HomeSync™, Apple TV™, or Google TV™), game consoles (e.g., Xbox™ and PlayStation™), electronic dictionaries, electronic keys, camcorders, electronic picture frames, and the like.

According to various embodiments, the electronic device may include at least one of medical devices (e.g., various portable medical measurement devices (e.g., a blood glucose monitoring device, a heartbeat measuring device, a blood pressure measuring device, a body temperature measuring device, and the like), a magnetic resonance angiography (MRA) device, a magnetic resonance imaging (MRI) device, a computed tomography (CT) device, scanners, and ultrasonic devices), navigation devices, Global Navigation Satellite System (GNSS) receivers, event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller machines (ATMs), points of sales (POSs) terminals, or Internet of things (IoT) devices (e.g., light bulbs, various sensors, electric or gas meters, sprinkler devices, fire alarms, thermostats, street lamps, toasters, exercise equipment, hot water tanks, heaters, boilers, and the like).

According to various embodiments, the electronic device may include at least one of parts of furniture or buildings/structures, electronic boards, electronic signature receiving devices, projectors, or various measuring instruments (e.g., water meters, electricity meters, gas meters, or wave meters, and the like). The electronic device may be one of the above-described devices or a combination thereof. An electronic device according to various embodiments may be a flexible electronic device. Furthermore, an electronic device is not limited to the above-described electronic devices and may include other electronic devices and new electronic devices according to the development of new technologies.

Hereinafter, electronic devices according to various embodiments are described with reference to the accompanying drawings. The term "user" as used herein may refer to a person who uses an electronic device or may refer to a device (e.g., an artificial intelligence electronic device) that uses an electronic device.

Figure 1:
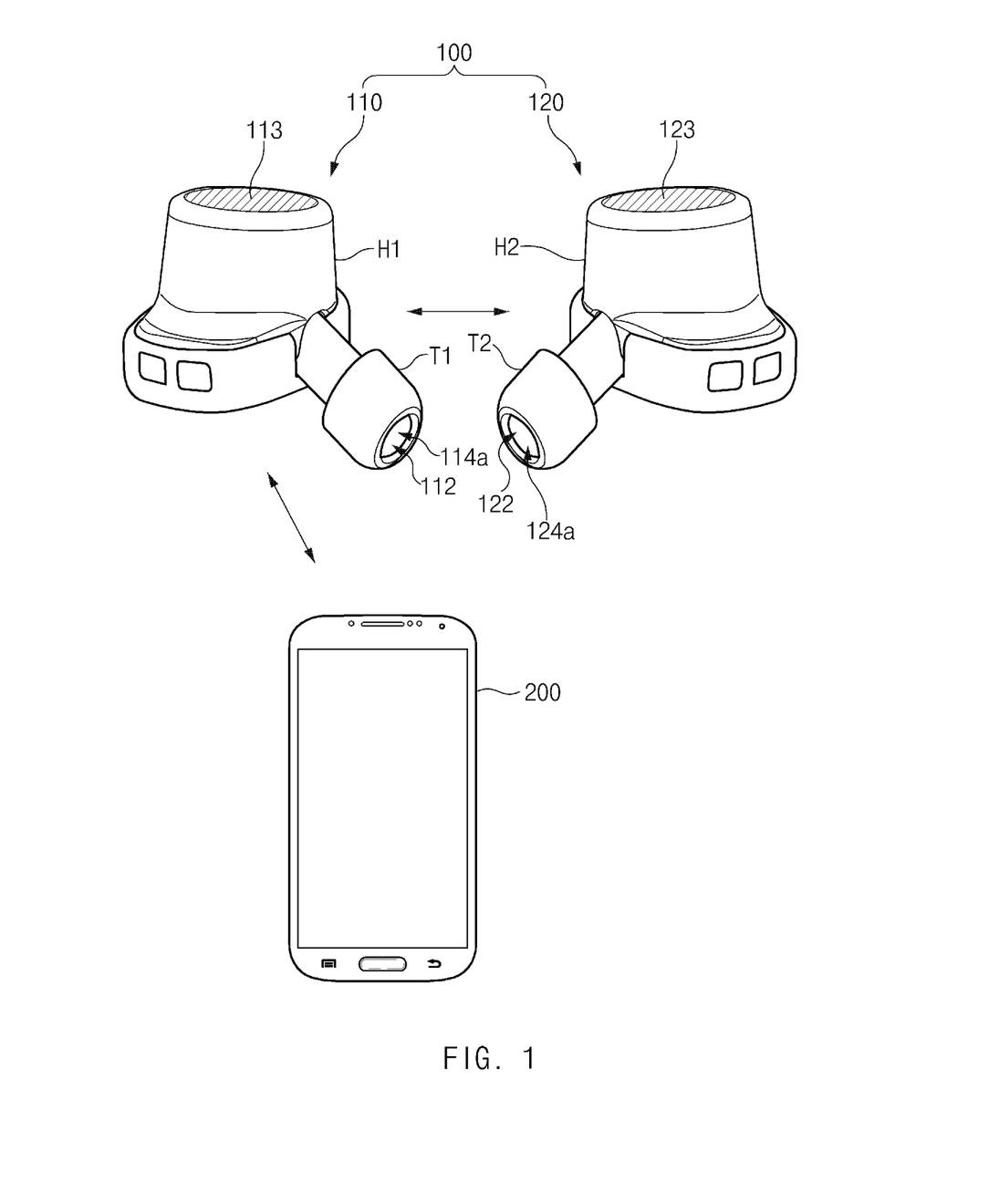
FIG. 1 illustrates an example of an audio output device with an external electronic device, according to an embodiment of the present disclosure.

FIG. 1 illustrates an example of an audio output device with an external electronic device, according to an embodiment of the present disclosure.

Referring to FIG. 1, an audio output device 100 includes a first output device 110 and a second output device 120. The first output device 110 is communicatively connected with an external electronic device 200 and the second output device 120.

The first output device 110 is mounted on one ear of a user and the second output device 120 is mounted on the other ear of the user. In FIG. 1, the audio output device 100 corresponds to earphones, i.e., the first output device 110 and the second output device 120, which are wirelessly connected to each other. However, embodiments of the present disclosure are not limited hereto. For example, the audio output device may be implemented as various forms of devices that are mounted on the user. For example, the audio output device may be earphones or a headphone in which the first and second output devices are physically connected to each other. The audio output device 100 is paired with the external electronic device 200.

The external electronic device 200 is a smartphone, but may be any type of electronic/mobile device, such as a tablet PC. The external electronic device 200 may output a voice received during a call with another electronic device or a sound whose source is stored in the external electronic device 200. The external electronic device 200 is paired with the audio output device 100.

The first output device 110 includes a housing H1, a tip T1, a speaker 112, a heart rate (HR) sensor 114a, and a touch pad 113. The housing H1 defines the appearance of the first output device 110. The tip T1 is coupled to an end portion of the housing H1. The tip T1 has a cylindrical shape formed from an elastic material which allows the first output device 100 to be securely attached to an ear of the user. The speaker 112 is arranged in the interior of the housing H1. The sound output from the speaker 112 is provided to an eardrum of the user through a hollow of the tip T1. The HR sensor 114a is also arranged in the interior of the housing H1. The HR sensor 114a emits infrared rays through the hollow of the tip T1 to detect a heart rate in the user's ear. The touch pad 113 detects the touch of the user's body.

The first output device 110 is wirelessly connected with the external electronic device 200. The first output device 110 is connected with the external electronic device 200 by using a first wireless communication scheme (e.g., Bluetooth scheme). When using Bluetooth or another master-slave scheme, the first output device 110 may operate as a master, and the external electronic device 200 may operate as a slave.

The first output device 110 may wirelessly connect with the external electronic device 200 when the user mounts the first output device 110 (or the second output device 120) on his/her ear. When the user mounts the first output device 110 may be determined based on the heart rate detected by the HR sensor 114a. When the first output device 110 is connected with the external electronic device 200, the first output device 110 may receive an audio signal, such as a voice or a sound source, which is output from the external electronic device 200. The first output device 110 may receive audio data in a streaming manner. The first output device 110 outputs the received audio data through the speaker 112 and sends the received audio data to the second output device 120. If a touch input is detected on the touch pad 113, the first output device 110 may perform a function, for example, play, stop, fast forward, rewind, volume control, call connection, or call end, corresponding to the touch input.

The second output device 120 includes the same elements as the first output device 110, namely, a housing H2, a tip T2, a speaker 122, a heart rate (HR) sensor 124a, and a touch pad 123. The second output device 120 wirelessly connects with the first output device 110 by using a second wireless communication scheme (e.g., Bluetooth scheme). In a Bluetooth or other master-slave scheme, the first output device 110 may operate as a master, and the second output device 120 may operate as a slave. The second output device 120 may be connected with the first output device 110 by using an advanced audio distribution profile (A2DP). The second output device 120 receives at least a portion of audio data from the first output device 110 through the second wireless communication scheme. The second output device 120 may receive the audio data in a streaming manner. The second output device 120 outputs the received audio data through the speaker 122 and if a touch input is detected on the touch pad 123, the second output device 120 may perform a function, for example, play, stop, fast forward, rewind, volume control, call connection, or call end, corresponding to the touch input.

Figure 2:
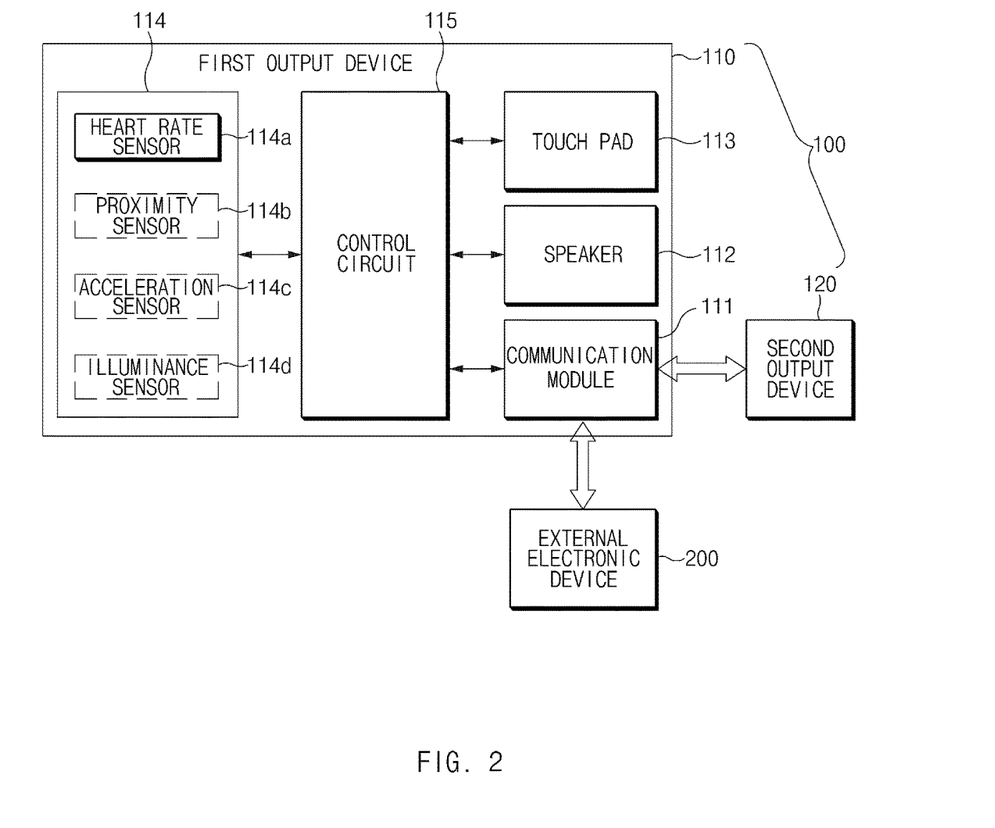
FIG. 2 is a block diagram of an audio output device, comprising a first and second output devices, with an external electronic device, according to an embodiment of the present disclosure.

FIG. 2 is a block diagram of an audio output device, according to an embodiment. In FIG. 2, the audio output device 100 includes the first output device 110 and the second output device 120, and the first output device 110 includes a communication module 111, the speaker 112, the touch pad 113, a sensor module 114, and a control module 115.

The communication module 111 communicates with the external electronic device 200. To do so, the communication module 111 may transmit or receive a wireless frequency signal through at least one antenna radiator. For example, the communication module 111 may include a short range communication module. The communication module 111 supports a short range communication scheme (e.g. Wireless-Fidelity (Wi-Fi), Bluetooth, near field communication (NFC), or the like) to communicate with the external electronic device 200.

The speaker 112 outputs sound. The output audio data may be received from, for example, the external electronic device 200. When the user mounts the first output device 110 on an ear, the speaker 112 outputs sound toward the inside of the user's ear.

The touch pad 113 detects a touch of the user's body upon it. The touch pad 113 is disposed so that when the user mounts the first output device 100 on the user's ear the user can still apply a touch input by using his/her finger.

The sensor module 114 includes one or more sensors that are capable of detecting whether the user wears the first output device 110. In FIG. 2, the sensor module 114 includes the HR sensor 114a, which emits infrared rays toward the inside of the user's ear and measures the heart rate by detecting the reflected infrared rays. The sensor module 114 in FIG. 2 further includes a proximity sensor 114b, an acceleration sensor 114c and an illuminance sensor 114d. The proximity sensor 114b detects the approach of an object to the first output device 110, the acceleration sensor 114c detects the acceleration of the first output device 110, and when the user wears the first output device 110, the illuminance sensor 114d detects the illuminance of the interior of the user's ear. The sensor module 114 may operate when the first output device 110 is deactivated or is not connected with the external electronic device 200.

The control circuit 115 is electrically connected with and controls the communication module 111, the speaker 112, the touch pad 113, and the sensor module 114. According to the embodiment in FIG. 2, when the mounting of the first output device 110 on the user's ear is detected, the control circuit 115 wirelessly connects the external electronic device 200 with the first output device 110 by using the communication module 111.

The control circuit may detect the mounting of an output device on the user's ear in a variety of ways, as would be understood by one of ordinary skill in the art. For example, the control circuit 115 may detect whether the first output device 110 is mounted based on data obtained by the HR sensor 114a. When a heart rate is first detected by the HR sensor 114a, the control circuit 115 may determine that the first output device 110 is mounted on the user's ear. The control circuit 115 may determine that the first output device 110 is mounted on user's ear when the heart rate is detected by the HR sensor 114a for a specified time period, or within a specified range. The control circuit 115 may detect/determine whether the first output device 110 is mounted based on data obtained by at least one of the acceleration sensor 114c, the illuminance sensor 114d, or the proximity sensor 114b or any combination of the HR sensor 114a, the proximity sensor 114b, the acceleration sensor 114c, or the illuminance sensor 114d. For example, when an acceleration of a specified range (e.g., a range of an acceleration that is applied when the user mounts the first output device 110 on an ear) is detected by the acceleration sensor 114c, and the heart rate is detected by the HR sensor 114a, the control circuit 115 may determine that the first output device 110 is mounted on the user's ear. As another example, when an illuminance of a specified range (e.g., a range of an illuminance that is detected in the interior of the user's ear) is detected by the illuminance sensor 114d, and the heart rate is detected by the HR sensor 114a, the control circuit 115 may determine that the first output device 110 is mounted on the user's ear. As yet another example, when the user is detected approaching by the proximity sensor 114b, and then the heart rate is detected by the HR sensor 114a, the control circuit 115 may determine that the first output device 110 is mounted on the user's ear.

When the mounting of the first output device 110 is detected by the sensor module 114, the control circuit 115 controls communication module 111 to wirelessly connect the external electronic device 200 with the first output device 110. When there is a connection history between the external electronic device 200 and the first output device 110, the external electronic device 200 may be automatically connected with the first output device 110.

The control circuit 115 receives audio data from the external electronic device 200 wirelessly. The audio data may include a voice or a sound source being output from the external electronic device 200. For example, the external electronic device 200 may output a voice from a call received from another electronic device, or the external electronic device 200 may output sound reproduced from a sound source file stored in the external electronic device 200. The control circuit 115 may receive audio data from the external electronic device 200 by using a streaming scheme. The control circuit 115 controls speaker 112 to output audio data.

The control circuit 115 sends at least a portion of audio data to the second output device 120 through wireless communication. The first output device 110 is connected with the second output device 120 through another path (the second wireless communication scheme) that is different from the path of wireless communication used to connect the first output device 110 with the external electronic device 200 (the first wireless communication scheme). The first and/or second communication scheme may be a Bluetooth scheme or an A2DP scheme. When the mounting of the first output device 110 is detected by the first output device 110, the first output device 110 is paired with the second output device 120. A portion of the received audio data is output by the first output device 110, and any other portion of the received audio data is output by the second output device 120. The control circuit 115 may send a portion of audio data, or all of the audio data, to the second output device 120.

According to an embodiment, the control circuit 115 sends data obtained by a heart rate sensor to the external electronic device 200 through wireless communication. The external electronic device 200 may utilize the heart rate data collected by the first output device 110.

According to an embodiment, the control circuit 115 performs a function corresponding to a touch input detected on the touch pad 113. The control circuit 115 may activate the touch pad 113 a specified time period after the mounting of the audio output device 100 is detected. The control circuit 115 may also output a notification signal by using the speaker 112 or a vibration motor electrically connected with the control circuit 115 after the specified time period. Operations in which the touch pad 113 is used are described below in detail with reference to FIG. 4.

According to an embodiment, when the demounting of the first output device 110 is detected, the control circuit 115 stops outputting audio data. The demounting may be detected in a number of ways. For example, if the heart rate is not detected by the HR sensor 114a for a specified time period, the control circuit 115 may determine that the first output device 110 is demounted from the user's ear. As another example, when an acceleration of a specified range (e.g., a range of an acceleration that is applied when the user demounts the first output device 110 from an ear) is detected by the acceleration sensor 114c or no acceleration is detected by the acceleration sensor 114c, the control circuit 115 may determine that the first output device 110 is demounted from the user's ear. As another example, when an illuminance of a specified range (e.g., a range of an illuminance higher than an illuminance that is detected in the interior of the user's ear) is detected by the illuminance sensor 114d, the control circuit 115 may determine that the first output device 110 is demounted from the user's ear. As another example, when the user is not detected by the proximity sensor 114b, the control circuit 115 may determine that the first output device 110 is demounted from the user's ear.

If it is determined that the first output device 110 is demounted from the user's ear, the control circuit 115 stops outputting audio data and releases the connection between the first output device 110 and the external electronic device 200.

The second output device 120 may include components like those in the first output device 110, such as a communication module, a speaker, a touch pad, and a control circuit. The communication module, the speaker, the touch pad, and the control circuit of the second output device 120 may perform functions similar to functions of the communication module 111, the speaker 112, the touch pad 113, and the control circuit 115 of the first output device 110, respectively. The communication module of the second output device 120 may communicate with the first output device 110 through another path (the second wireless communication scheme) that is different from the path of wireless communication used to connect the first output device 110 with the external electronic device 200 (the first wireless communication scheme). The first and/or second communication schemes may be any short range communication scheme, such as Wi-Fi Direct, Bluetooth, NFC, A2DP, or the like.

According to an embodiment, when the mounting of the first output device 110 is detected by the sensor module 114, the control circuit of the second output device 120 may receive at least a portion of audio data from the first output device 110 through the second wireless communication. The control circuit may output the at least a portion of the received audio data by using the speaker.

According to an embodiment, the control circuit of the second output device 120 may perform a function corresponding to a touch input detected by the touch pad of the second output device 120. If the mounting of the first output device 110 is detected, the control circuit may activate the touch pad after a specified time. The control circuit may output a notification signal by using the speaker or a vibration motor electrically connected with the control circuit after the specified time.

The external electronic device 200 may also output a voice or a sound source by using a speaker included in the external electronic device 200. When the external electronic device 200 is paired with the first output device 110, the external electronic device 200 may provide the first output device 110 with audio data associated with a voice or a sound source that is being output. If the connection between the external electronic device 200 and the first output device 110 is released, the external electronic device 200 may continue to output the voice or a sound source, which was being output by using the first output device 110, by using the speaker of the external electronic device 200.

Figure 3:
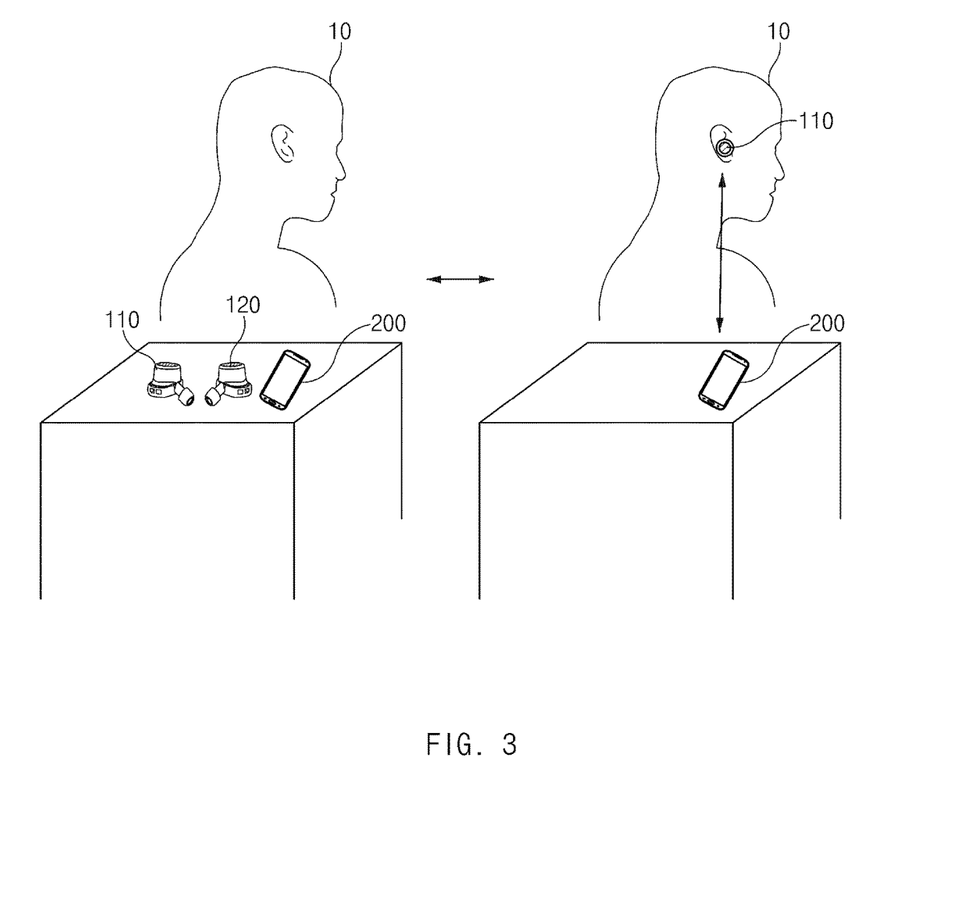
FIG. 3 illustrates an example of how an audio output device may be mounted on a user, according to an embodiment of the present disclosure.

FIG. 3 illustrates an example of how an audio output device may be mounted on a user, according to an embodiment. Specifically, one of the audio output devices 110 and 120 is mounted on each ear of a user 10. The audio output devices 110 and 120 may also be demounted from the ears of the user 10.

According to an embodiment, when the user 10 mounts the audio output devices 110 and 120 on his/her ears, an output path for the audio data may be changed. Whether the audio output devices 110 and 120 are mounted may be determined by using a sensor module (e.g., the sensor module 114 of FIG. 2). If it is determined that the audio output devices 110 and 120 are mounted, the audio output devices 110 and 120 are activated. For example, the state of each of the audio output devices 110 and 120 may be switched from an idle state to a busy state. Each of the audio output devices 110 and 120 may activate a communication module and one or both may be automatically connected with the external electronic device 200. The external electronic device 200 may be on a phone call with another electronic device or may be playing a sound source stored in the external electronic device 200. The external electronic device 200 may output a call voice or a sound source by using the speaker included in the external electronic device 200. When the external electronic device 200 is subsequently connected with the audio output devices 110 and 120, the external electronic device 200 may provide the audio data associated with a call voice or a sound source to the audio output devices 110 and 120 and may stop outputting the call voice or the sound source on its own speaker.

According to an embodiment, when the audio output devices 110 and 120 are demounted from the ears of the user 10, the output path of the audio data may be changed. The audio output devices 110 and 120 may determine whether the audio output devices 110 and 120 are demounted by using a sensor module (e.g., the sensor module 114 of FIG. 2). If it is determined that the audio output device 110 and 120 are demounted from the user's ears, the audio output device 110 and 120 may release the connection with the external electronic device 200 or may themselves be deactivated. For example, each of the audio output devices 110 and 120 may switch from the busy state to the idle state. The audio output devices 110 and 120 may release the connection with the external electronic device 200 by deactivating the communication module(s). If the connection is released, the call voice or the sound source that is being output by the audio output devices 110 and 120 may continue to be output by the external electronic device 200. If the connection is released, the output of the call voice or the sound source may be stopped.

Figure 4:
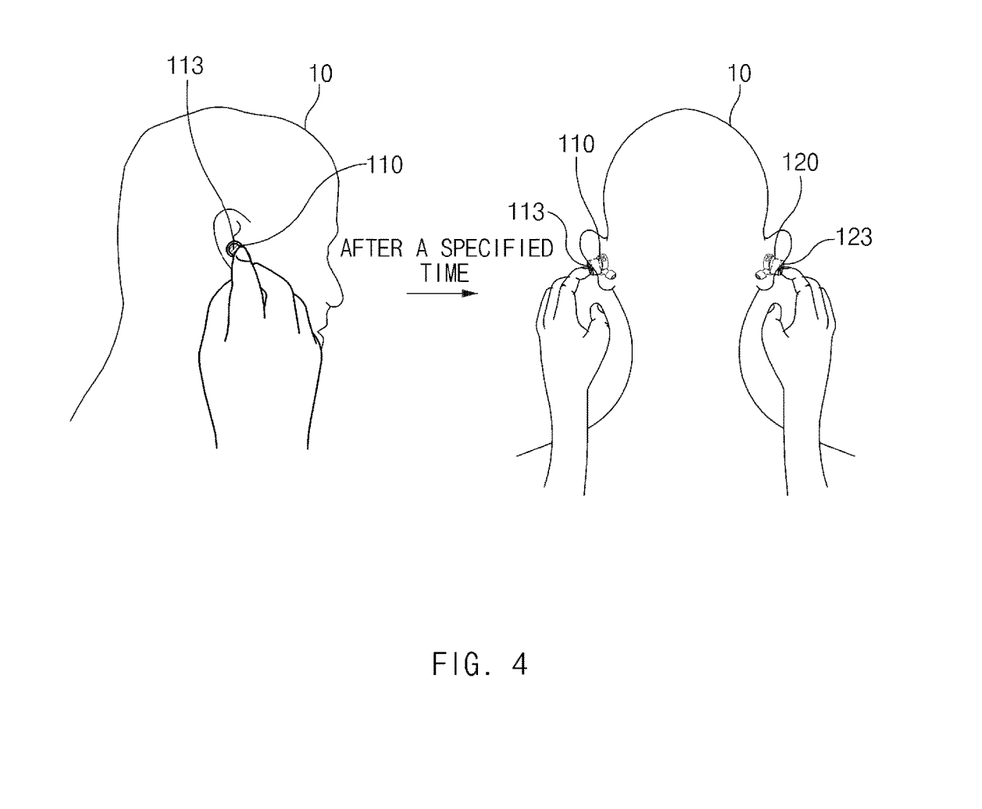
FIG. 4 illustrates an example of how an audio output device may be used, according to an embodiment of the present disclosure.

FIG. 4 illustrates an example of how an audio output device may be used, according to an embodiment.

Referring to FIG. 4, the audio output devices 110 and 120 are mounted on the ears of the user 10 by the user 10 using a hand of the user 10. During normal operation, when the touch pad 113 detects a touch input of the user 10, the audio output devices 110 and 120 perform a function corresponding to the touch input. For example, the audio output devices 110 and 120 may perform a function such as, for example, play, stop, fast forward, rewind, volume control, call connection, or call end, based on the duration of the touch input, the number of touch inputs, an input interval of the touch input. As another example, when the touch input is detected, the audio output devices 110 and 120 may obtain data associated with the touch input and send the obtained data to an external electronic device (e.g., the external electronic device 200) which may perform the function, for example, play, stop, fast forward, rewind, volume control, call connection, or call end, based on the data associated with the touch input.

However, before normal operation, during the process where the user 10 mounts the audio output devices 110 and 120 on his/her ears, the hand of the user 10 may touch the touch pad 113 or 123 included in the audio output device 110 or 120, respectively. Therefore, a wrong input that the user 10 does not intend may occur.

According to an embodiment, to prevent the above-described wrong input, the audio output devices 110 and 120 activate the touch pads 113 and 123 a specified time after the audio output devices 110 and 120 are mounted on the ears of the user10. For example, the audio output devices 110 and 120 may activate the touch pad 113 and 123 three seconds after the audio output devices 110 and 120 are activated or are connected with the external electronic device. According to an embodiment, the audio output devices 110 and 120 output a notification signal using a speaker or a vibration motor after a specified time period, such as three seconds, after the audio output devices 110 and 120 are activated or are connected with the external electronic device.

According to various embodiments, the audio output devices 110 and 120 may include various push types of input buttons. To protect the wrong input to the input button(s), the audio output devices 110 and 120 may activate the input button(s) a specified time after the user 10 mounts the audio output devices 110 and 120 on his/her ears.

Figure 5:
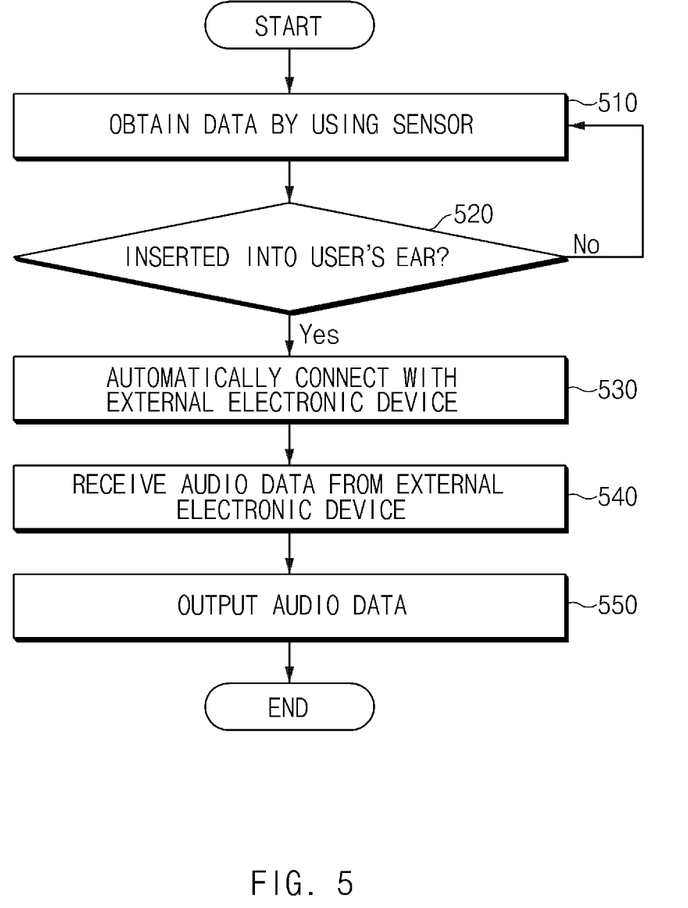
FIG. 5 is a flowchart of an operating method of an audio output device, according to an embodiment of the present disclosure.

FIG. 5 is a flowchart of an operating method of an audio output device, according to an embodiment. The flowchart in FIG. 5 may include any operations that the audio output device illustrated in FIGS. 1 to 4 performs. Therefore, contents describing the audio output device in FIGS. 1 to 4 may be applied to the flowchart shown in FIG. 5 even though those contents are omitted below.

Referring to FIG. 5, in step 510, the audio output device (e.g., the control circuit 115 in audio output device 100) obtains data by using a sensor (e.g., the sensor module 114). For example, even if the audio output device 100 is not connected with an external electronic device (e.g., the external electronic device 200) or is deactivated, the audio output device 100 supplies power to the sensor to obtain data associated with a heart rate, acceleration, illuminance, proximity (e.g., whether an object is approaching), or the like by using the sensor.

In step 520, the audio output device (e.g., the control circuit 115) determines whether the user is currently inserting the audio output device into his/her ear. For example, when the change in the heart rate, the proximity of an object, acceleration, illuminance, or the like is detected, the audio output device may determine that the audio output device is being inserted into the user's ear based on the detection of the heart rate, the proximity of the object, acceleration, illuminance, or the like.

If the audio output device is detected being inserted into the user's ear in step 530, the audio output device is automatically connected with the external electronic device (e.g., by the control circuit 115).

In step 540, the audio output device (e.g., the control circuit 115) receives audio data from the external electronic device. For example, the audio output device may receive audio data corresponding to a voice call or a sound source, which is being output by the external electronic device, from the external electronic device in a streaming manner.

In step 550, the audio output device (e.g., the control circuit 115) outputs the audio data by using the speaker included in the audio output device in real time.

Figure 6:
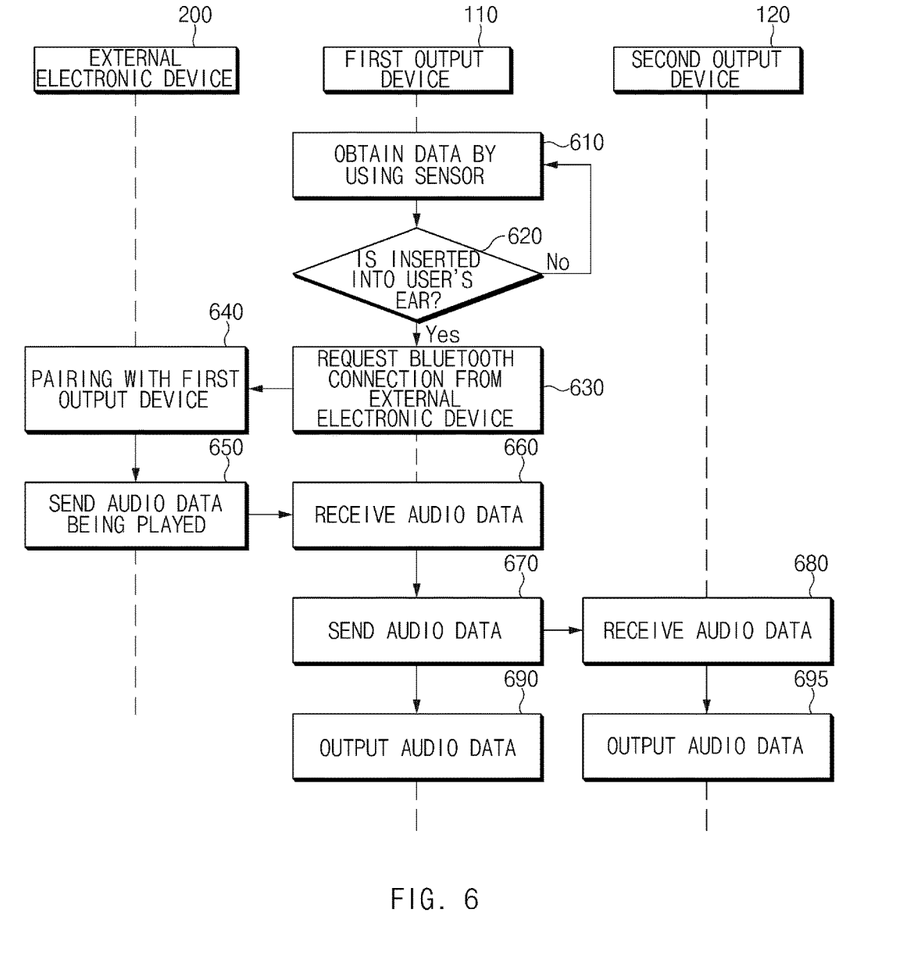
FIG. 6 is a flowchart of an operating method of an audio output device, according to an embodiment of the present disclosure.

FIG. 6 is a flowchart of an operating method of an audio output device, according to an embodiment. For convenience, descriptions about operations that are substantially the same as previously described operations are not duplicated. The flowchart in FIG. 6 may include any operations that the audio output device illustrated in FIGS. 1 to 4 performs. Therefore, contents describing the audio output device in FIGS. 1 to 4 may be applied to the flowchart shown in FIG. 6 even though those contents are omitted below.

Referring to FIG. 6, in step 610, the first output device (e.g., the control circuit 115) obtains data by using a sensor.

In step 620, the first output device (e.g., the control circuit 115) determines whether the first output device is inserted into a user's ear.

When the first output device is detected being inserted into the user's ear in step 630, the first output device (e.g., the control circuit 115) requests a Bluetooth connection from the external electronic device. The external electronic device may have a connection history with the first output device.

In step 640, the external electronic device is paired with the first output device in response to the request of the first output device. In some embodiments, even though not illustrated in FIG. 6, if the first output device is detected being inserted into the user's ear, the first output device also requests connection with/from the second output device and then is paired with the second output device.

In step 650, the external electronic device sends audio data, which is being played by the external electronic device, to the first output device. For example, the external electronic device may send audio data corresponding to a voice call or a sound source which is currently being played to the first output device 110 in real time.

In step 660, the first output device (e.g., the control circuit 115) receives the audio data from the external electronic device.

In step 670, the first output device (e.g., the control circuit 115) sends the audio data to the second output device. For example, the first output device may send all or a portion of the audio data received from the external electronic device to the second output device in real time.

In step 680, the second output device receives the audio data from the first output device. For example, the second output device may receive all or a portion of the audio data by A2DP in real time.

In step 690, the first output device (e.g., the control circuit 115) outputs the audio data. The first output device outputs audio data which is time-synchronized with the second output device together with the second output device.

In step 695, the second output device outputs the audio data. Although shown in FIG. 6 as a separate operation, the second output device 120 outputs the audio data to be time-synchronized with the first output device, i.e., together with the first output device 110 performing step 690.

According to various embodiments of the present disclosure, the usability of the audio output device may be improved by automatically connecting with the external electronic device when the mounting of the audio output device by the user is detected.

Furthermore, the wrong input to the touch pad may be prevented by activating the touch pad a specified time after the mounting by the user.

The term "module" as used herein may represent, for example, a unit including one or more combinations of hardware, software and firmware. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" may include at least one of an application-specific integrated circuit (IC) (ASIC) chip, a field-programmable gate array (FPGA), and a programmable-logic device for performing some operations, which are known or will be developed.

At least a part of an apparatus (e.g., modules or functions thereof) or a method (e.g., operations) according to various embodiments of the present disclosure may be, for example, implemented by instructions stored in a computer-readable storage media in the form of a program module. The instructions, when executed by one or more processors, may cause the one or more processors to perform a function corresponding to the instructions. The computer-readable storage media, for example, may be a memory.

The computer-readable storage medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), and hardware devices (e.g., a read only memory (ROM), a random access memory (RAM), or a flash memory). Also, the program instruction may include not only a mechanical code such as is generated by a compiler but also a high-level language code executable on a computer using an interpreter. The above hardware unit may be configured to operate via one or more software modules for performing an operation of the present disclosure, and vice versa.

A module or a program module according to various embodiments may include at least one of the above elements, or a part of the above elements may be omitted, or additional other elements may be further included. Operations performed by a module, a program module, or other elements according to various embodiments may be executed sequentially, in parallel, repeatedly, or in a heuristic method. In addition, some operations may be executed in different sequences or may be omitted. Alternatively, other operations may be added.

Besides, a variety of effects directly or indirectly understood through this disclosure may be provided.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An audio output device comprising:
    a communication circuit to communicate with an external electronic device;
    a speaker;
    an acceleration sensor;
    a proximity sensor; and
    a controller electrically coupled with the communication circuit, the speaker, the acceleration sensor, and the proximity sensor, wherein the controller is configured to:
        obtain acceleration data using the acceleration sensor;
        detect a proximity of an external object with respect to the audio output device using the proximity sensor, based at least in part on a determination that the obtained acceleration data satisfies a specified acceleration condition;
        establish a wireless connection between the audio output device and the external electronic device using the communication circuit, based at least in part on a determination that the proximity satisfies a specified proximity condition;
        receive audio data from the external electronic device via the wireless connection; and
        output a sound via the speaker based at least in part on the audio data.

2. The audio output device of claim 1, wherein the controller is configured to:
    receive, as at least part of the audio data, audio data corresponding to a sound source being output by the external electronic device via the wireless connection.

3. The audio output device of claim 1, wherein the controller is configured to:
    stop outputting the sound based at least in part on a determination that the audio output device is not mounted to a user of the audio output device.

4. The audio output device of claim 3, wherein the controller is configured to:
    release the wireless connection based at least in part on a determination that the audio output device is not mounted to the user of the audio output device.

5. The audio output device of claim 1, wherein the controller is configured to:
    establish another wireless connection between the audio output device and another audio output device using the communication circuit; and
    transmit at least a portion of data associated with the sound to the other audio output device via the other wireless connection.

6. The audio output device of claim 1, wherein the controller is configured to:
    receive a user input to control the outputting of the sound; and
    transmit control data corresponding to the user input to the external electronic device via the wireless connection.

7. The audio output device of claim 6, further comprising a touch pad electrically connected with the controller, wherein the controller is configured to:
    activate the touch pad based at least in part on the determination that the proximity satisfies the specified proximity condition; and
    perform the receiving of the user input using the touch pad.

8. The audio output device of claim 1, wherein the controller is configured to:
    output via the speaker, a notification indicating that the wireless connection is established.

9. The audio output device of claim 1, wherein the controller is configured to:
    automatically perform the establishing of the wireless connection, based at least in part on a determination that the external electronic device was previously connected to the audio output device.

10. The audio output device of claim 1, wherein the controller is configured to:
    activate the acceleration sensor at least temporarily while the audio output device is disconnected from the external electronic device.

11. An audio output device comprising:
    a speaker;
    an acceleration sensor;
    a proximity sensor;
    a communication circuit to communicate with an external electronic device; and
    a controller, wherein the controller is configured to:
        detect that the audio output is mounted on a user of the audio output device using the acceleration sensor and the proximity sensor;
        establish a wireless connection between the audio output device and the external electronic device using the communication circuit, based at least in part on a determination that the audio output device is mounted on the user;
        receive audio data corresponding to a sound source being output by the external electronic device via the wireless connection; and
        output a sound, via the speaker, based at least in part on the audio data.

12. The audio output device of claim 11, wherein the controller is configured to:
    stop outputting the sound based at least in part on a determination that the audio output device is not mounted to the user.

13. The audio output device of claim 11, wherein the controller is configured to:
    release the wireless connection based at least in part on a determination that the audio output device is not mounted to the user.

14. The audio output device of claim 11, wherein the controller is configured to:
    establish another wireless connection between the audio output device and another audio output device using the communication circuit; and transmit at least a portion of data associated with the audio data to the other audio output device via the other wireless connection.

15. The audio output device of claim 11, wherein the controller is configured to:
receive a user input to control the outputting of the sound; and
transmit control data corresponding to the user input to the external electronic device via the wireless connection.

16. The audio output device of claim 15, further comprising a touch pad electrically connected with the controller, wherein the controller is configured to:
activate the touch pad based at least in part on the determination that the audio output is mounted on the user; and
perform the receiving of the user input using the touch pad.

17. The audio output device of claim 11, wherein the controller is configured to output, via the speaker, a notification indicating that the wireless connection is established.

18. An audio output device comprising:
a first sensor;
a second sensor;
a communication circuit configured to communicate with an external electronic device;
a speaker configured to output sound; and
a controller, wherein the controller is configured to:
obtain first sensing data using the first sensor;
obtain second sensing data using the second sensor based at least in part on a determination that the first sensing data satisfies a first specified condition;
determine that the audio output device is mounted on a user of the audio output device based at least on a determination that the second sensing data satisfies a second specified condition; and
establish a wireless connection between the audio output device and the external electronic device using the communication circuit, based at least in part on the determination that the audio output device is mounted on the user and another determination that the external electronic device has been connected to the audio output device.

19. The audio output device of claim 18, wherein the controller is configured to:
receive audio data from the external electronic device via the wireless connection;
output a sound, via the speaker, based at least in part on the audio data.

20. The audio output device of claim 18, wherein the controller is configured to:
receive a user input to control the outputting of the sound; and
transmit control data corresponding to the user input to the external electronic device via the wireless connection.

* * * * *